US005179022A

United States Patent [19]

Sanford et al.

[11] Patent Number: 5,179,022

[45] Date of Patent: Jan. 12, 1993

[54] BIOLISTIC APPARATUS FOR DELIVERING SUBSTANCES INTO CELLS AND TISSUES IN A NON-LETHAL MANNER

[75] Inventors: John C. Sanford, Geneva; Edward D. Wolf, Ithaca; Nelson K. Allen, Newfield, all of N.Y.

[73] Assignee: E. I. Du Pont de Nemours & Co., Wilmington, Del.

[21] Appl. No.: 833,822

[22] Filed: Feb. 11, 1992

Related U.S. Application Data

[63] Continuation of Ser. No. 727,287, Jul. 5, 1991, abandoned, which is a continuation of Ser. No. 161,807, Feb. 29, 1988, abandoned.

[51] Int. Cl.[5] ......................... C12M 1/00; A61M 5/30

[52] U.S. Cl. ................................ 435/287; 435/172.1; 435/172.3; 935/52; 935/85; 604/69; 89/1.14

[58] Field of Search ............................... 435/284-287, 435/172.1, 172.3; 953/52, 53, 85; 128/740; 604/68-70; 73/11, 12, 167; 124/60; 102/501, 502, 508-510; 89/1.14

[56] References Cited

U.S. PATENT DOCUMENTS

| | | | |
|---|---|---|---|
| 3,130,575 | 4/1964 | Rogers | 73/167 |
| 3,343,400 | 9/1967 | Rogers et al. | 73/167 |
| 3,404,599 | 10/1968 | Annis | 73/12 |
| 4,664,664 | 5/1987 | Drake, Jr. | 102/502 |
| 4,833,961 | 5/1989 | Adini | 102/502 |
| 4,945,050 | 7/1990 | Sanford et al. | 435/172.1 |
| 5,036,006 | 7/1991 | Sanford et al. | 435/172.1 |

FOREIGN PATENT DOCUMENTS 0270356 6/1988 European Pat. Off. .

OTHER PUBLICATIONS

Sanford et al. "Delivery of Substances into Cells and Tissues Using a Particle Bombardment Process," Particulate Science and Technology, vol. 5 (1987), pp. 27-37.

*Primary Examiner*—Robert J. Warden
*Assistant Examiner*—William A. Beisner
*Attorney, Agent, or Firm*—Sughrue, Mion, Zinn, Macpeak & Seas

[57] ABSTRACT

An apparatus for delivering substances into living cells and tissues includes an impeller of the type adapted to use an explosive charge for sending a macroprojectile through an accelerator passage into a vacuum chamber. The vacuum chamber is divided into an upper vacuum chamber having an impact receiving plate against which the macroprojectile will impact and a lower vacuum chamber in which the biological material to be impregnated by the substance is located. The substance may be carried by a plurality of microprojectiles adhered to the base of the macroprojectile so that upon impact of the macroprojectile against the impact plate in the upper vacuum chamber the microprojectiles carrying the substance will pass through an aperture in the impact plate and enter the biological material. Alternatively, the microprojectiles carrying the substance may be mounted on the surface of the impact plate facing the biological material so that upon impact of the macroprojectile against the impact plate, the microprojectiles will be impelled into the biological material.

9 Claims, 4 Drawing Sheets

FIG.4a
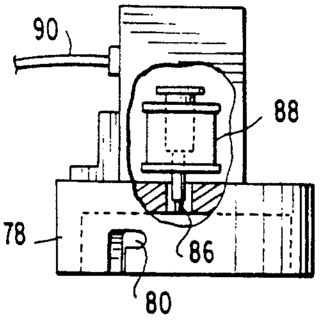
FIG.4b
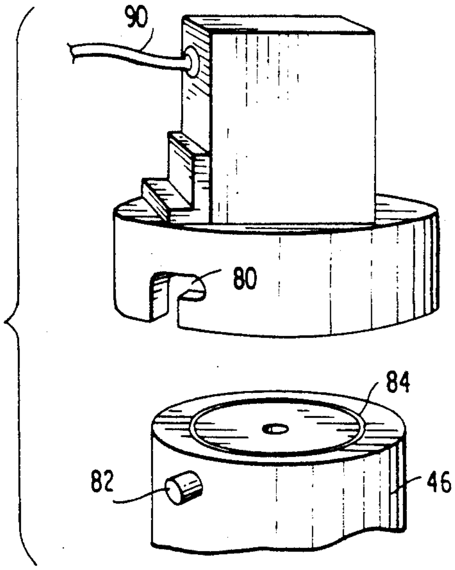
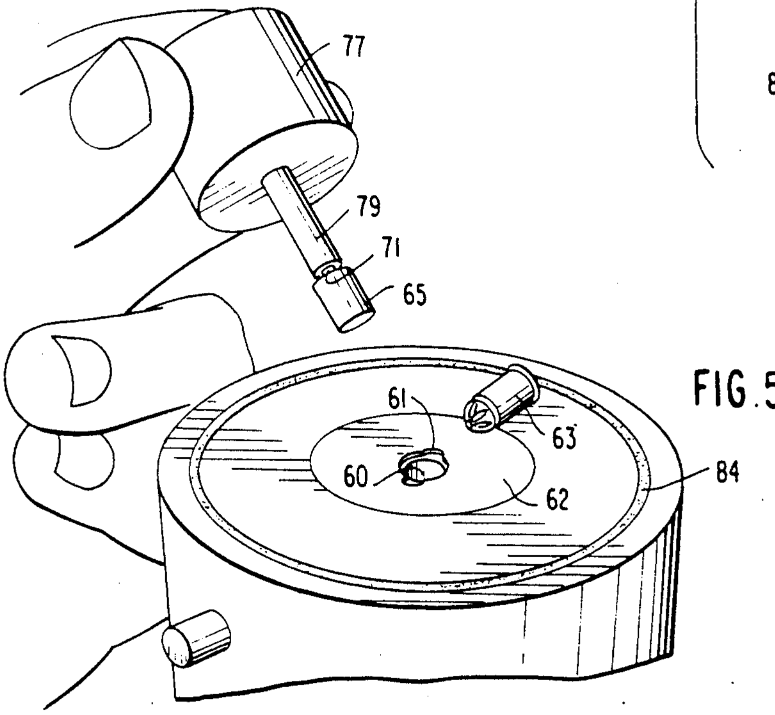
FIG.5
FIG.6
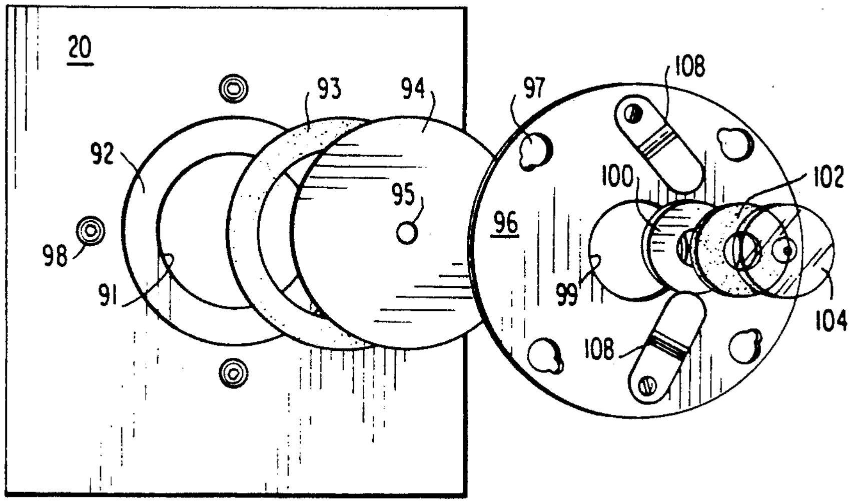

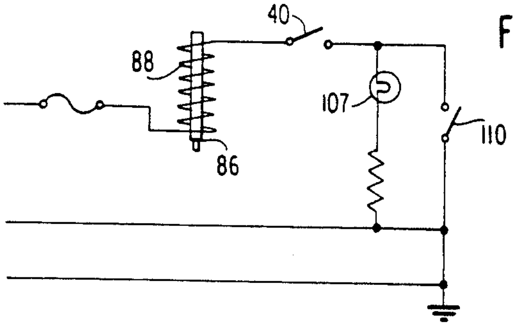
FIG.7
FIG.8a
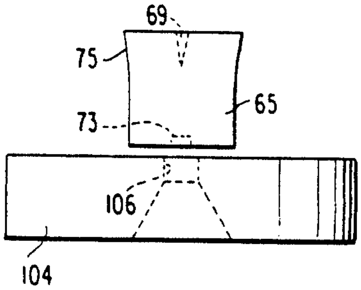
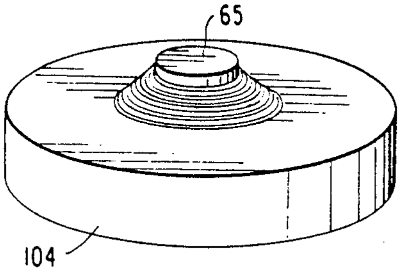
FIG.8b
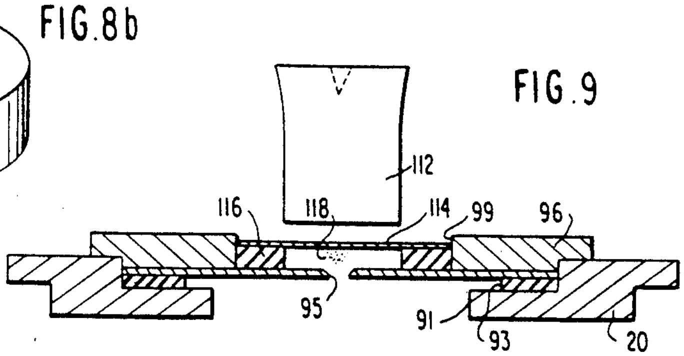
FIG.9
FIG.11
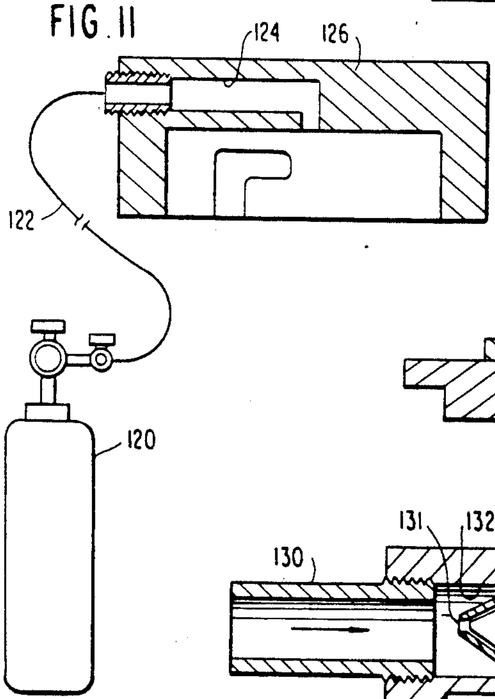
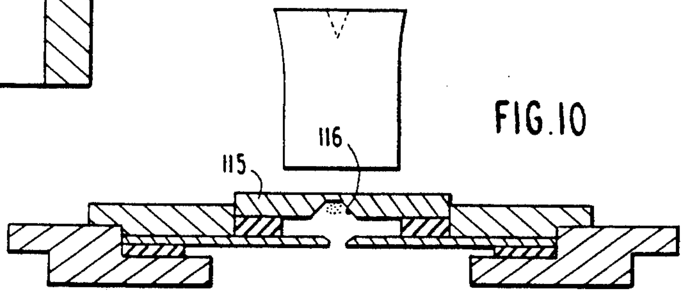
FIG.10
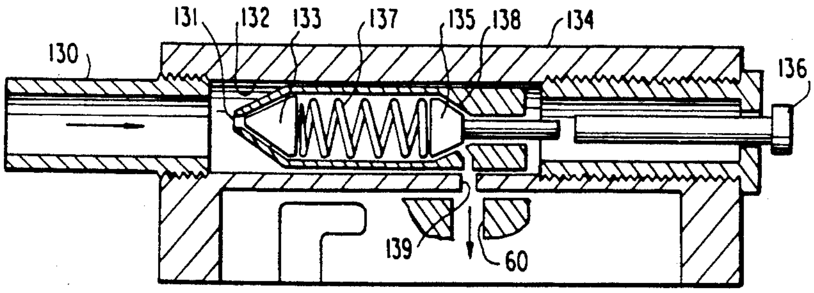
FIG.12

BIOLISTIC APPARATUS FOR DELIVERING SUBSTANCES INTO CELLS AND TISSUES IN A NON-LETHAL MANNER

This is a continuation of application Ser. No. 07/727,287 filed Jul. 5, 1991, now abandoned, which is a continuation of application Ser. No. 07.161,807 filed Feb. 29, 1988, now abandoned.

BACKGROUND OF THE INVENTION

The present invention is directed to a particle bombardment system for delivering substances into living cells and tissues and more specifically, to an apparatus for accelerating microprojectiles carrying these substances into a vacuum chamber containing the cells and tissues to be penetrated by the substances without contamination or lethal damage of the living cells and tissues by the specific means used to accelerate the microprojectiles.

The named inventors of the present application are also the named inventors of copending U.S. patent application Ser. No. 877,619 filed Jun. 23, 1986, now abandoned, which is a Continuation-in-Part of application Ser. No. 670,771 filed Nov. 13, 1984, now U.S. Pat. No. 4,945,050, which is directed to a "Method for Transporting Substances Into Living Cells and Tissues and Apparatus Therefor". The biolistic process disclosed in these applications is a new and unique method for delivering substances into living cells and tissues.

Needleless hypodermic injectors are old and well known in the art for introducing substances into tissues but not into cells. The U.S. Patent to Clark et al. (U.S. Pat. No. 3,853,125) discloses such a disposable needleless injector which includes a medicament containing ampule, a container of pressurized gas and a connection operatively coupling the gas to the ampule to pressurize the medicament for discharge. The ampule includes at least one rigid end wall which is provided with an opening therein which serves as a discharge orifice through which the pressurized medicament is discharged in the form of a high pressure injection stream. The opposite end of the ampule is configured to permit the medicament to be rapidly pressurized by the gas.

The U.S. patent to Schwebel et al. (U.S. Pat. No. 4,124,024) is also directed to a disposable hypodermic injection ampule for performing needleless percutaneous injections. A propellant charge in one end of the device is exploded by means of a firing pin and the explosive gases drive a plunger to pressurize the fluid injectant and force it outwardly of the device through a discharge orifice.

The U.S. patent to Tsujino (U.S. Pat. No. 3,515,130) is directed to a jet-injection hypodermic device which consists essentially of a hydraulically operated injector, hydraulic pressure means connected to and supplying hydraulic pressure to the injector and hand operated control means to control the hydraulic pressure. The injector comprises an injector head containing a piston pump for drawing in injection liquid through an inlet and ejecting the liquid through a fine ejection orifice. The hydraulic piston is driven in one direction for ejecting the injection fluid by hydraulic pressure and in the opposite direction for drawing in injection liquid by a return spring.

SUMMARY OF THE INVENTION

The present invention provides a new and improved apparatus for the delivery of substances into living cells and tissues in a more efficient manner, while minimizing the risk of damage or contamination of the living cells and tissues by extraneous materials.

The present invention provides a new and improved apparatus for the delivery of substances into living cells and tissues comprising housing means having a vacuum chamber therein, partition means dividing said vacuum chamber into an upper vacuum chamber and lower vacuum chamber, said partition means having resiliently mounted impact means, barrel means detachably connected to said housing means and having an acceleration passage therein disposed in alignment with said impact receiving means and accelerating means detachably mounted at the opposite end of said barrel means for imparting acceleration to a macroprojectile along said acceleration passage into contact with said impact receiving means for accelerating microprojectile means having a desired substance thereon into an object mounted in said lower vacuum chamber. The microprojectile means may be carried by said macroprojectile means for delivery through an aperture in said impact receiving means when said macroprojectile impacts against said impact receiving means or may be mounted on the side of said impact receiving means facing said lower vacuum chamber whereby the force of said macroprojectile impacting against said impact receiving means will accelerate said microprojectile means toward the object in said lower vacuum chamber. The accelerating means may be comprised of means for firing an explosive charge for imparting acceleration to a macroprojectile located in said acceleration passage or may be comprised of means for controlling the flow of a gas under pressure to said accelerator passage for imparting acceleration directly to microprojectiles in said acceleration passage for impact directly on an object located in said vacuum chamber.

The foregoing and other objects, features and advantages of the invention will be apparent from the following more particular description of a preferred embodiment of the invention as illustrated in the accompanying drawings.

FIG. **3*a*** is an exploded view showing the lower end of the barrel positioned above the vacuum chamber with the impact receiving plate visible within the vacuum chamber.

FIG. **3*b*** is an exploded perspective view showing the lower end of the barrel positioned above the vacuum chamber.

FIG. **4*a*** is a side elevation view, partly in section showing a first embodiment of an accelerating mechanism.

FIG. **4*b* is an exploded view showing the relationship of the accelerating mechanism of FIG. 4*a*** relative to the upper end of the barrel.

FIG. 5 is a perspective view showing the upper end of the barrel with a macroprojectile and an explosive device prior to insertion in the acceleration passage.

FIG. 6 is an exploded view of the impact support assembly adapted to be located in the vacuum chamber.

FIG. 7 is a circuit diagram for the solenoid driven firing pin.

FIG. 8*a* is a side elevation view of a macroprojectile and stopping plate, according to the present invention.

FIG. 8*b* is a perspective view of the microprojectile and stopping plate of FIG. 8*a* after impact.

FIG. 9 is a sectional side elevation view of a modified form of an impact transfer assembly.

FIG. 10 is a sectional side elevation view of a further modified impact transfer mechanism according to the present invention.

FIG. 11 is a side elevational view, partly in section, of a second embodiment of an accelerating mechanism according to the present invention.

FIG. 12 is a schematic view, partly in section, of a third embodiment of an accelerating mechanism.

DETAILED DESCRIPTION OF THE INVENTION

Figure 1:
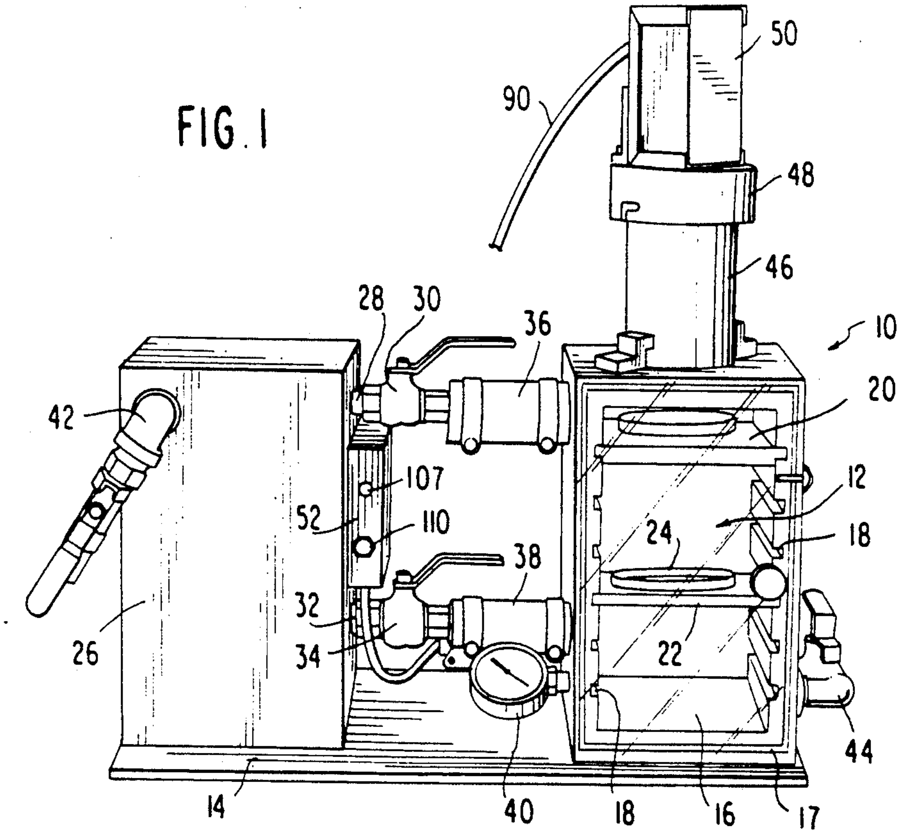
FIG. 1 is a front perspective view of the apparatus according to the present invention.
Figure 2:
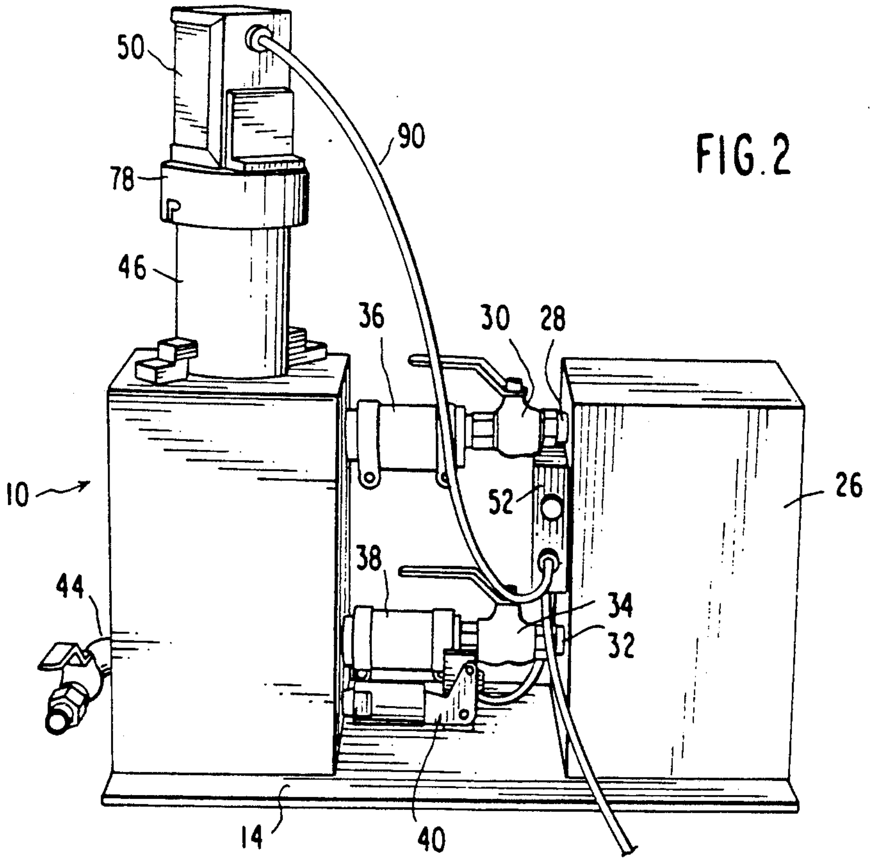
FIG. 2 is a rear perspective view of the apparatus as shown in FIG. 1.

An overall view of the apparatus according to the present invention is shown in FIG. 1. A housing 10 defining a vacuum chamber 12 is located at one end of a support platform 14 and is provided with a transparent door 16 hinged along one side of the chamber. A gasket 17 is secured about the entire periphery of the opening for engagement by the door in the closed position to provide a vacuum-tight seal. A plurality of grooves 18 are formed on opposite sides of the chamber for adjustably supporting a pair of shelves 20 and 22 at various positions within the chamber 12. The shelf 20 is adapted to divide the vacuum chamber 12 into an upper vacuum chamber and a lower vacuum chamber and supports a macroprojectile impact assembly which will be described hereinafter.

The lower shelf 22 merely provides a support for a sample holder 24 which may contain living cells or tissues for bombardment by a plurality of microprojectiles. A surge chamber 20 is located within a second housing 26 mounted adjacent the first housing 10 at the opposite end of the support plate 14. A first conduit 28 having a suitable on-off valve 30 is connected between the surge chamber and the upper vacuum chamber and a second conduit 32 having a suitable valve 34 is connected between the surge chamber 26 and the lower vacuum chamber. Suitable filters 36 and 38 may be provided in the conduits 28 and 32 respectively to prevent the transfer of any contaminants from the upper vacuum chamber to the lower vacuum chamber through the surge chamber 26. A pressure operated switch mechanism 40 of conventional design, is connected through the wall of the housing 10 and is responsive to the pressure within the vacuum chamber 12. A fitting 42 is connected with the interior of the surge chamber 26 for connecting the chamber 26 to a suitable vacuum pump (not shown). Another fitting 44 having a manually controlled valve is connected to the interior of the lower vacuum chamber for venting the chamber to the atmosphere subsequent to the impregnation of the biological material.

An acceleration barrel 46 having an acceleration passage which will be described hereinafter, is connected to the top of the housing 10. In the embodiment shown, an explosive charge is adapted to be placed at the top of the barrel and a cover 48 carrying a solenoid operated firing mechanism 50 is secured to the upper end of the barrel 46. A control box 52 is mounted on the side of the surge chamber 26 and is electrically connected to the pressure operator switch 40, a source of power (not shown) and the solenoid operated firing mechanism 50, the details of which will be set forth hereinafter.

Figure 3A:
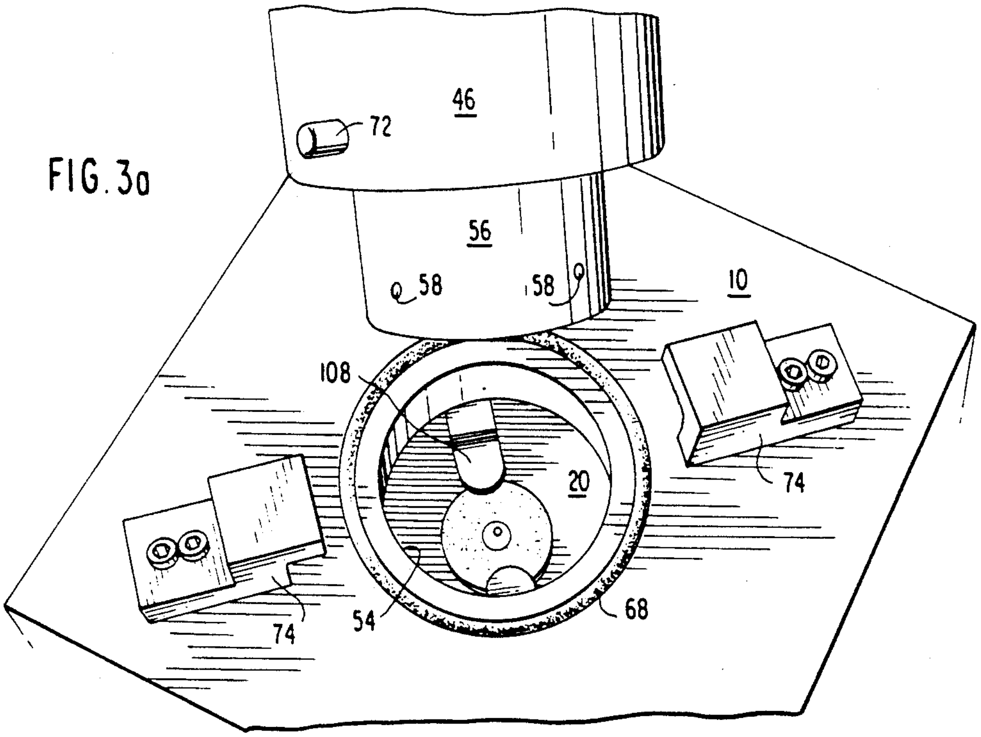
Figure 3B:
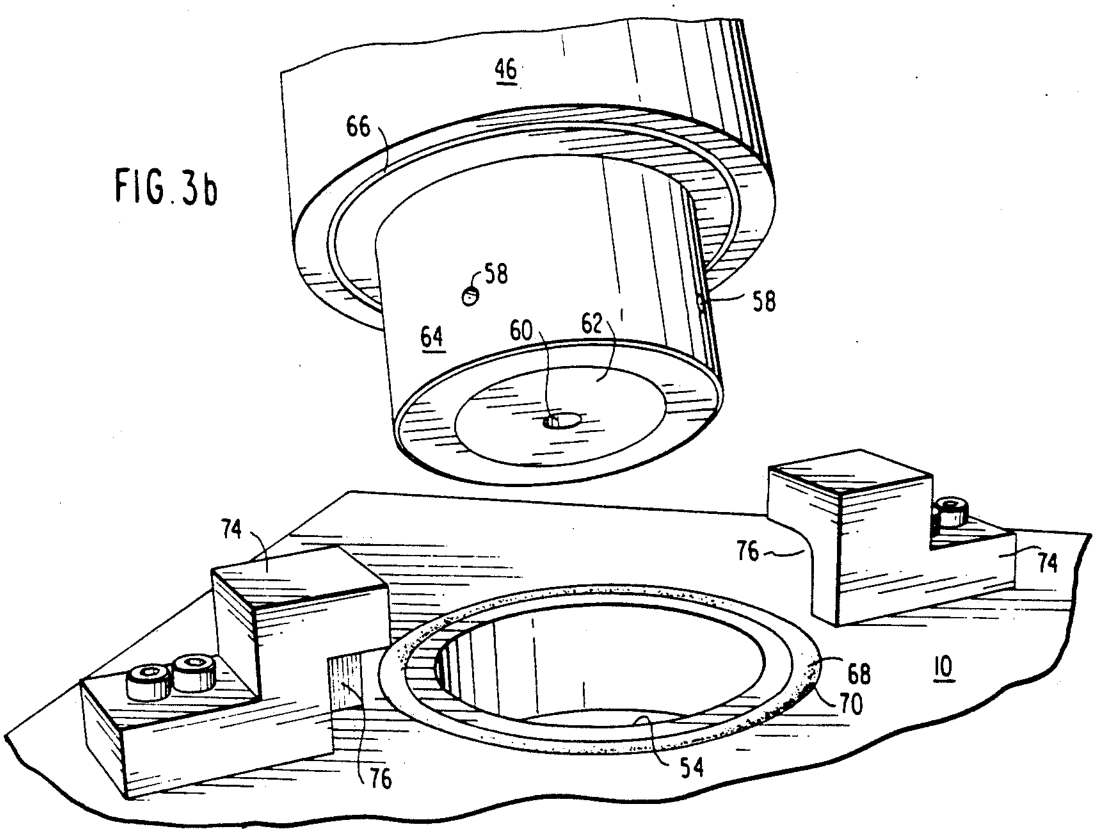

FIG. 3 shows the upper end of the housing 10 with the lower end of the barrel removed from the aperture 54 in the top of the housing 10. The barrel 46 is provided with a reduced diameter lower end 56 having a plurality of radially disposed vent passages 58 disposed in communication with the acceleration passage 60. The acceleration passage 60 is formed concentrically within a cylindrical core 62 of stainless steel, which is surrounded by a thick aluminum cladding 64. A sealing groove 66 is provided in the lower end of the larger diameter portion of the barrel 46 for cooperation with a sealing ring 68 of elastimeric material disposed in an annular groove 70 concentric with the bore 54 in the top of the housing 10. The lower end of the large diameter portion of the cylinder 46 is provided with a pair of diametrically opposed pins 72, only one of which is shown in FIG. 3*a*, which cooperate with a pair of locking blocks 74 provided with oppositely directed recesses 76 which engage with the pins 72 to provide a twist-lock connection between the barrel and the housing. The support plate 20 for the impact receiving device is visible through the bore 54 in the top of the housing 10.

A top plate or cap 78 for the upper end of the barrel 46 is shown in FIGS. 4*a* and 4*b*. The plate 78 is provided with a downwardly extending skirt having a pair of diametrically opposed, oppositely directed notches 80 for cooperating with diametrically opposed pins 82 extending radially outwardly from the top end of the barrel 46. The pins and notches provide a twist-lock connection between the top plate and the barrel and a sealing ring 84 is provided in the upper surface of the barrel 46 for cooperation with the plate 78 to provide an air-tight connection. A solenoid operated firing pin 86 is mounted on the top surface of the top plate 78 with the coil 88 electrically connected to the control box 52 by means of a wire 90.

A macroprojectile 65, as shown in FIGS. 5 and 8, is in the form of a substantially cylindrical plug made of LEXAN (polycarbonate), high density polyethylene or similar low-density materials with high cohesive strength. The macroprojectiles must be of low density to reduce their momentum at impact, making it easier to stop them without releasing too much energy. Too much energy dissipation generates high velocity debris from both the macroprojectile and the stopping plate. High cohesive strength is needed to prevent shattering which would cause excessive high velocity debris damage to cells and tissues. Partial melting and deformation is desirable while excessive melting or vaporization will generate debris. The shape of the macroprojectile should allow for molded manufacture, easy loading into the acceleration passage 60, while still giving the projectile 65 a very tight fit in the passage 60. Tightness of fit is needed to allow high compression behind the projectile which allows for complete burn where gunpowder is employed and to prevent "blow by" of gasses or debris around the macroprojectile, since the material might damage the biological material on the front of the macroprojectile or might be accelerated in front of the microprojectiles into the lower vacuum chamber causing damage to cells or tissue. The macroprojectile shape should minimize mass while preserving cohesive strength and should have sufficient length to prevent tumbling during acceleration prior to impacting on the stopping plate which will be described hereinafter.

The macroprojectile should hold and center a plurality of microprojectiles on its front surface and a recess 73, as shown in FIG. 8*a*, has been provided for this purpose. To allow for easy loading, an expanded or flared rear end portion 75 is provided on the macroprojectile and a tapered recess 69 is provided in the rear surface to reduce mass and allow the driving force to expand the sidewalls of the macroprojectiles outward and ensure a tight fit within the passage 60. For certain situations, metal faced macroprojectiles and metal stopping plates can be used.

In order to facilitate loading of the macroprojectile into the bore 60, a loading tool as shown in FIG. 5 is provided having a cylindrical handle 77, a small diameter rod 79 extending therefrom and having a tapered pin 71 on the forward end thereof. Thus, the pin can be force fitted into the tapered recess 69 for picking up the macroprojectile 65 and inserting it into the acceleration passage 60. The length of the rod 79 is such that when it is pushed fully into the passage 60 with the cylindrical handle 77 engaging the upper surface of the barrel, there will remain just enough room in the acceleration passage for the insertion of an explosive charge 63, which is in the form of an ordinary gun powder cartridge without a projectile on the end thereof. An explosive charge 63 is inserted into the passage 60 and diametrically opposed recesses 61 are provided at the top end of the passage 60 to facilitate in the insertion and removal of the explosive charge 63. The end of the explosive charge 63 will be flush with the upper surface of the barrel so that when the top plate is secured on the end of the barrel, the firing pin 86 will be disposed in close proximity to the end of the explosive charge 63.

The impact receiving device is best shown in FIG. 6, but is also seen in conjunction with the vacuum chamber in FIGS. 1 and 3*a*. The plate 20, which is adapted to be adjustably disposed within the vacuum chamber 12 to divide the vacuum chamber into the upper vacuum chamber and the lower vacuum chamber, is provided with a central aperture 91 having an annular recess 92 extended about the aperture 91 for the reception of an elastomeric ring 93. A support disk 94 having a central aperture 95 has a diameter approximately equal to the diameter of the elastomeric ring 93 and is adapted to be superimposed thereon. The locking plate 96, having a plurality of elongated slotted apertures 97 disposed about the periphery thereof, is adapted to rest on the support disk 94 with the headed pins 98 extending into and locking the locking plate 96 to the plate 20 by means of a twist-lock operation. The locking plate 96 is provided with a central aperture 99 which is substantially larger than the aperture 95 and disposed coaxial therewith. An annular plate of spring steel 100 is fitted within the aperture 99 with an annular ring of elastomeric material 102 superimposed thereon. The impact or stopping plate 104 is in the form of a disposable disk 104 made of LEXAN (polycarbonate) or a similar material which absorbs the energy of the macroprojectile 65 through permanent deformation in a manner which is uniquely suited for dissipating large amounts of ballistic energy without shattering. The plate 104 is provided with an aperture in the center thereof which is sized relative to the macroprojectile 65 and a recess 73 in which the microprojectiles are located, so that the plate 104 will stop the macroprojectile 65 while permitted the microprojectiles to pass through the aperture 106 in the plate 104 as best seen in FIG. 8*a*. The aperture or hole 106 tapers outwardly on the opposite side of the plate 104 to achieve better dispersion of the microprojectiles toward the biological material carried in the dish 24 within the lower vacuum chamber. The plate 104, the elastimeric ring 102 and the spring disk 100, are secured in place relative to the locking plate 96 by means of a pair of pivoted spring arms 108. As the macroprojectile deforms against the plate 104 it will completely fill and close the aperture 106 as shown in FIG. 8*b* to completely seal off the upper vacuum chamber from the lower vacuum chamber and prevent the passage of explosive debris or impact debris from passing through the plate 20 into the lower chamber where the biological material is located.

A complete operative cycle of operation of the apparatus will now be described. A valve 44 is opened to place the interior of the housing 10 at atmospheric pressure, thereby allowing the door 16 to be opened. The dish 24 containing the biological material which is to be impregnated with a desired substance such as DNA material, is placed on the adjustable support plate 22 which is perforated so that the portion of the chamber above and below the support plate 22 will be at the same pressure. A new stopping plate 104 is secured to the impact receiving mechanism mounted on the plate 20 which is upwardly positioned within the housing 10 to divide the interior of the housing 10 into an upper vacuum chamber and a lower vacuum chamber. The door 16 is then closed and latched and the valve 44 is closed to cut off the interior of the housing 10 from the atmosphere. The barrel 46 is secured to the upper surface of the housing 10 by means of a twist-lock connection with the acceleration passage 60 of the barrel disposed in alignment with the aperture 106 in the stopping plate 104. The microprojectiles carrying the substance which is to be impregnated into the biological tissue is then placed in a recess 73 in the bottom of a macroprojectile 65. The macroprojectile 65 with the microprojectiles adhered thereto is then loaded into the barrel by means of the tool, as shown in FIG. 5. An explosive cartridge 63 is then inserted into the upper end of the acceleration passage 60 and the top plate 78 is secured to the upper end of the barrel by means of the twist-lock connection. The valves 30 and 34 are moved to the open position interconnecting the upper and lower vacuum chambers with the surge chamber 26. A vacuum pump or other suitable source of vacuum is connected to the fitting 42 and operated to reduce the pressure within the vacuum chambers and the surge chamber. When the vacuum in the upper and lower vacuum chambers reaches a predetermined value, the vacuum operated switch 40 shown in FIGS. 1 and 7, will close. At this time the solenoid operated firing pin will not be operated but the arming light 107 will be turned on, indicating that the apparatus is ready for firing. The valve 34 is then closed to isolate the lower vacuum chamber containing the biological substance to be impregnated from the upper vacuum chamber which will contain explosive debris after the firing takes place. The firing switch 110 is then closed to activate the solenoid driven firing pin which will detonate the explosive charge 63 and drive the macroprojectile 65 through the acceleration passage, whereupon it will impact against the stopping plate 104. The inertia of the macroprojectile 65 will be absorbed by the stopping mechanism shown in FIG. 6 and the microprojectiles carrying the desired substance will be accelerated through the opening 106 into the biological material in the dish 24. The sudden surge of high pressure within the upper vacuum chamber can be absorbed by the surge chamber 26 and any debris will be trapped in the filter 36. The source of vacuum can then be deactivated, the valve 44 opened to communicate the interior of the housing 10 with the atmosphere and the door 16 opened to remove the dish containing the impregnated biological material.

An alternative method of stopping the macroprojectile and launching microprojectiles is shown in FIG. 9. The macroprojectile 112 is similar in all respects to the macroprojectile 65 described previously, with the exception that the macroprojectile 112 is not provided with any means for carrying the microprojectiles. The plate 20, the elastomeric ring 93, the disk 94 and the locking plate 96 are substantially identical to the corresponding elements previously described with respect to FIG. 6. However, in the central aperture 99 of the locking plate 96, a thin lightweight disk 114 is supported on an elastomeric ring 116 with the coated microprojectiles 118 adhered to the surface thereof opposite the surface against which the macroprojectile 112 will impact. The thin plate should be of very low mass so that the velocity of the combined macroprojectile and the thin disk after impact is as near as possible to the impact velocity of the macroprojectile. Thus, the microprojectiles will be accelerated from the disk 114 through the aperture 94 and impact on the biological material in the lower vacuum chamber. In the embodiment of FIG. 9, the disk is constructed of titanium. In the embodiment of FIG. 10, a locally thin disk of LEXAN (polycarbonate). 115 having a recess 16 for the reception of the microprojectiles is utilized in lieu of the titanium disk 114. In both of these embodiments, as well as in the first embodiment, using the apertured stopping plate, the complete sealing will take place between the upper vacuum chamber and the lower vacuum chamber so as to prevent the passage of extraneous material such as explosive debris which would contaminate or damage the biological material in the lower vacuum chamber.

While the explosive charge illustrated in the first embodiment is substantially the same as a cartridge used in a gun which is fired upon impact of a firing pin, in any case, the firing will be electrically controlled using a circuit similar to that shown in FIG. 7 for activating the firing pin. The safety switch, or pressure operated switch can be set to any desired pressure threshold. This arrangement provides a safety mechanism which only allows firing when there is some degree of vacuum in the chamber, thereby preventing the firing of the explosive charge when the door is open, or when the barrel is disassembled, thus ensuring that no high velocity material can escape from the apparatus and cause personal injury.

In addition to utilizing an explosive type acceleration force generator, it is possible to air, helium or other like gasses as a driving force. The advantage of compressed gas over an explosive charge as an energy source is that it is cleaner, can be used as a blast or alternatively as a continuous-feed stream, and can be used to accelerate either macroprojectiles, which is turn will accelerate microprojectiles, or accelerate microprojectiles directly. It is well known that light gasses such as helium accelerate into areas of reduced pressure at much greater velocities than heavier gasses such as air, due to their greater mean kinetic energy at a given temperature. A continuous stream of high pressure helium can be provided into the acceleration barrel in the manner shown in FIG. 11. The tank of compressed gas 120 is connected by suitable tubing 122 to a passage 124 in the top plate 126 which will communicate directly into the acceleration passage 60 when the top plate 126 is secured to the upper end of the barrel by means of the twist-lock connection. Alternatively, short bursts of helium can be provided to the acceleration barrel through a rapid release valve mechanism such as that shown in FIG. 12. Such a mechanism is employed in commercially available pellet guns and includes a connector 130 adapted to be connected to a source of gas under pressure. The connector supplies the pressurized gas to a passage 132 within the top plate 134. A pair of valve members 133 and 135 are disposed within the passage and are normally biased by means of the spring 137 into engagement with the valve seats 131 and 138 to prevent the passage of compressed gas through the aperture 139 into the acceleration barrel. When gas is supplied to passage 132, the valve 133 opens to admit gas into the chamber containing spring 137. Upon depression of the hammer 136, the valve member 135 will be moved to the open position against the force of the spring 137 to allow a burst of pressurized gas into the acceleration passage 60 when the top plate 134 is secured to the top of the barrel by the twist-lock connection.

While the invention has been particularly shown and described with reference to preferred embodiments thereof, it will be understood by those in the art that the foregoing and other changes in form and details may be made therein without departing from the spirit and scope of the invention.

What is claimed is:

1. An apparatus for the delivery of a substance into living cells and tissues comprising:

housing means defining a vacuum chamber therein and having a top wall;

connecting means for connecting said vacuum chamber to a source of vacuum;

a horizontally disposed partition in said vacuum chamber dividing said chamber into an upper vacuum chamber and a lower vacuum chamber and having an aperture therein;

a single closure means on said housing means for providing simultaneous access to said upper and lower chambers;

support means for horizontally supporting said partition in any one of a plurality of positions in said chamber;

shelf means adjustably supported on said support means in said lower chamber for holding a biological sample below said partition;

aperture means defining an aperture in said top wall of said housing;

impelling means connected to said housing means and aligned with said aperture means for imparting an impelling force to a substance; and impact receiving means mounted in said aperture in said partition for directing the substance into the biological sample in said lower vacuum chamber while dissipating forces generated by said impelling means in said upper vacuum chamber.

2. An apparatus as set forth in claim 1, wherein said impelling means comprises barrel means connected to said housing means and having an upper end, a large diameter portion engaging said top wall and a reduced diameter portion extending through said aperture means in said top wall into said upper vacuum chamber, accelerator passage means defining a passage extending through said barrel means and having an upper end, a macroprojectile positioned in said accelerator passage means adjacent said upper end of said passage, an explosive charge extending into said upper end of said passage means and sealing said upper end of said passage means, cover means connected to said upper end of said barrel means and electrically operated firing means carried by said cover means for igniting the explosive charge in the upper end of said passage means.

3. An apparatus as set forth in claim 2, further comprising control circuit means connected to said firing means and including pressure responsive switch means in communication with said lower vacuum chamber and manual firing switch means electrically connected in series with said firing means and said pressure responsive switch means.

4. An apparatus as set forth in claim 2, wherein said impact receiving means comprises a disposable disk having a central aperture therethrough, said central aperture having a diameter less than the diameter of said macroprojectile, said macroprojectile further comprising carrying means on an end remote from said explosive charge for carrying a plurality of microprojectiles coated with the substance to be delivered into the biological sample, mounting means for resiliently mounting said disk on said partition in alignment with the aperture in said partition and in alignment with said accelerator passage means such that when the explosive charge is ignited, the macroprojectile will be impelled along said accelerator passage means and impact on said disk in an area surrounding the central aperture thereof permitting the microprojectiles to continue through said central aperture into the biological sample located in said lower vacuum chamber with the macroprojectile being deformed to block and seal said central aperture.

5. An apparatus as set forth in claim 2, wherein said impelling means further comprises microprojectiles coated with the substance to be delivered into the biological sample, a disk having said microprojectiles adhered to one surface thereof, means for resiliently supporting said disk over the aperture in said partition with said microprojectiles facing into the lower vacuum chamber above the biological sample to be impregnated such that when the explosive charge is ignited, the macroprojectile will be impelled along said accelerator passage means into engagement with said disk thereby transferring energy from the macroprojectile to the microprojectiles and impelling them into the biological substance.

6. An apparatus as set forth in claim 1, wherein said impelling means comprises barrel means connected to said housing means and having an upper end, a large diameter portion engaging said top wall and a reduced diameter portion extending through said aperture means in said top wall into upper vacuum chamber, accelerator passage means defining a passage extending through said barrel means and having an upper end, a macroprojectile positioned in said accelerator passage means adjacent said upper end of said passage, cover means connected to said upper end of said barrel means and having a gas passage extending therethrough with an inlet end in fluid communication with a source of pressurized gas and an outlet end in fluid communication with said accelerator passage means.

7. An apparatus as set forth in claim 6, further comprising valve means in communication with said gas passage for controlling the flow of pressurized gas so as to provide a short burst of pressurized gas to impel the macroprojectile through said accelerator passage means into engagement with said impact receiving means.

8. An apparatus as set forth in claim 1, wherein said impact receiving means is comprised of a disk adapted to have micro-projectiles coated with a substance to be injected into a biological substance adhered to one surface thereof and means for resiliently supporting said disk over the aperture in said partition with the micro-projectiles facing into the lower vacuum chamber above a biological sample to be impregnated whereby the impelling force causes said impact receiving means to transfer energy to the micro-projectiles and impel them into the biological substance.

9. An apparatus for the delivery of a substance into living cells and tissues comprising:

housing means defining a vacuum chamber therein and having a top wall;

a horizontally disposed partition in said vacuum chamber dividing said chamber into an upper vacuum chamber and a lower vacuum chamber and having an aperture therein;

support means for horizontally supporting said partition in said chamber;

shelf means in said lower chamber for holding a biological sample below said partition;

aperture means defining an aperture in said top wall of said housing;

impelling means connected to said housing means and extending into said aperture means for imparting an impelling force to a substance;

impact receiving means mounted in said aperture in said partition for directing the substance into the biological sample in said lower vacuum chamber while dissipating forces generated by said impelling means in said upper vacuum chamber;

surge tank means connected to a source of vacuum;

first conduit means having first shut off valve means interconnected between said surge tank means and said upper vacuum chamber; and second conduit means having second shut off valve means interconnected between said surge tank means and said lower vacuum chamber, such that when said first shut off valve means and said second shut off valve means are in an open position, said upper and lower vacuum chambers and said surge tank means are evacuated and when said first shut off valve means is in an open position and said second shut off valve means is in a closed position the forces generated by the impelling means are dissipated to said surge tank means.

* * * * *